(12) United States Patent
Nathan et al.

(10) Patent No.: US 7,005,136 B2
(45) Date of Patent: Feb. 28, 2006

(54) BONE REPLACEMENT MATERIALS UTILIZING BIOABSORBABLE LIQUID POLYMERS

(75) Inventors: Aruna Nathan, Bridgewater, NJ (US); Mora C. Melican, Bridgewater, NJ (US); Kelly R. Brown, Hillsborough, NJ (US); Mark C. Zimmerman, East Brunswick, NJ (US)

(73) Assignee: Ethicon, Inc., Somerville, NJ (US)

( * ) Notice: Subject to any disclaimer, the term of this patent is extended or adjusted under 35 U.S.C. 154(b) by 273 days.

(21) Appl. No.: 10/112,554

(22) Filed: Mar. 29, 2002

(65) Prior Publication Data

US 2003/0185871 A1 Oct. 2, 2003

(51) Int. Cl.
*A61F 2/00* (2006.01)
(52) U.S. Cl. ...................... 424/423; 424/422
(58) Field of Classification Search ................ 424/423
See application file for complete search history.

(56) References Cited

U.S. PATENT DOCUMENTS

| | | | |
|---|---|---|---|
| 2,895,930 A | 7/1959 | Milton | |
| 3,806,479 A | 4/1974 | Cunningham et al. | |
| 3,978,203 A | 8/1976 | Wise | |
| 3,997,512 A * | 12/1976 | Casey et al. ................ | 528/285 |
| 4,048,256 A | 9/1977 | Casey et al. | |
| 4,076,798 A | 2/1978 | Casey et al. | |
| 4,095,600 A | 6/1978 | Casey et al. | |
| 4,118,470 A | 10/1978 | Casey et al. | |
| 4,122,129 A | 10/1978 | Casey et al. | |
| 4,384,975 A | 5/1983 | Fong | |
| 4,419,139 A | 12/1983 | Gooch et al. | |
| 4,568,559 A | 2/1986 | Nuwayser et al. | |
| 5,137,743 A * | 8/1992 | Zaks et al. .................. | 426/602 |
| 5,155,246 A | 10/1992 | Naskar et al. | |
| 5,219,980 A | 6/1993 | Swidler | |
| 5,306,311 A | 4/1994 | Stone et al. | |
| 5,360,626 A | 11/1994 | Iyengar et al. | |
| 5,411,554 A | 5/1995 | Scopelianos et al. | |
| 5,442,033 A | 8/1995 | Bezwada et al. | |
| 5,464,929 A | 11/1995 | Bezwada et al. | |
| 5,599,852 A | 2/1997 | Scopelianos et al. | |
| 5,607,687 A * | 3/1997 | Bezwada et al. ........... | 424/426 |
| 5,618,552 A | 4/1997 | Bezwada et al. | |
| 5,628,993 A | 5/1997 | Yamagata et al. | |
| 5,631,015 A | 5/1997 | Bezwada et al. | |
| 5,653,992 A | 8/1997 | Bezwada et al. | |
| 5,670,478 A | 9/1997 | Stuchlik et al. | |
| 5,698,213 A | 12/1997 | Jamiolkowski et al. | |
| 5,700,583 A | 12/1997 | Jamiolkowski et al. | |
| 5,725,881 A | 3/1998 | Buchholz et al. | |
| 5,728,752 A | 3/1998 | Scopelianos et al. | |
| 5,750,100 A | 5/1998 | Yamagata et al. | |
| 5,753,234 A | 5/1998 | Lee et al. | |
| 5,824,333 A | 10/1998 | Scopelianos et al. | |
| 5,859,150 A | 1/1999 | Jamiolkowski et al. | |
| 5,998,552 A | 12/1999 | Gruber et al. | |
| 6,074,660 A | 6/2000 | Jamiolkowski et al. | |
| 6,100,346 A | 8/2000 | Jamiolkowski et al. | |
| 6,110,501 A | 8/2000 | Redding, Jr. et al. | |
| 6,114,458 A | 9/2000 | Hawker et al. | |
| 6,120,787 A | 9/2000 | Gustafsson et al. | |
| 6,121,398 A * | 9/2000 | Wool et al. ............... | 526/238.1 |
| 6,147,168 A | 11/2000 | Jamiolkowski et al. | |
| 6,224,894 B1 | 5/2001 | Jamiolkowski et al. | |
| 6,251,435 B1 | 6/2001 | Jamiolkowski et al. | |
| 6,268,329 B1 | 7/2001 | Markussen | |
| 6,335,383 B1 | 1/2002 | Scopelianos et al. | |
| 2001/0007771 A1 | 7/2001 | Sullivan et al. | |
| 2001/0021377 A1 | 9/2001 | Jamiolkowski et al. | |
| 2002/0037301 A1 | 3/2002 | De La Poterie | |
| 2003/0185752 A1 | 10/2003 | Nathan et al. | |

FOREIGN PATENT DOCUMENTS

| | | |
|---|---|---|
| EP | 0422209 B1 | 3/1995 |
| EP | 841361 A1 | 5/1995 |
| EP | 747072 A | 12/1996 |
| EP | 1270024 A | 1/2003 |
| WO | WO 88/03785 A1 | 6/1988 |
| WO | WO 89/08694 A1 | 9/1989 |
| WO | WO 90/12604 A1 | 11/1990 |
| WO | WO 92/12645 A1 | 8/1992 |
| WO | WO 93/08850 A1 | 5/1993 |
| WO | WO 94/25079 A1 | 11/1994 |
| WO | WO 94/15079 A1 | 11/1995 |
| WO | WO 95/33821 A1 | 12/1995 |
| WO | WO 97/09367 | 3/1997 |
| WO | WO 97/23606 A1 | 7/1997 |
| WO | WO 99/29303 A1 | 6/1999 |
| WO | WO 00/02950 A1 | 1/2000 |
| WO | WO 00/35511 A | 6/2000 |
| WO | WO 00/44808 A1 | 8/2000 |
| WO | WO 01/07486 A1 | 2/2001 |
| WO | WO 01/76649 A | 10/2001 |

OTHER PUBLICATIONS

U.S. Appl. No. 10/162,933, A. Nathan.
U.S. Appl. No. 10/178,970, A. Nathan.
U.S. Appl. No. 10/183,260, Rosenbatt et al.
U.S. Appl. No. 10/322,132, A. Nathan.
U.S. Appl. No. 10/322,177, S.C. Arnold.
U.S. Appl. No. 10/325,768, A. Nathan.

(Continued)

*Primary Examiner*—Gollamudi S. Kishore
*Assistant Examiner*—Eric E. Silverman

(57) ABSTRACT

The present invention is directed to bone replacement devices and compositions containing a synthetic, bioabsorbable, biocompatible liquid polymer that is the reaction product of a polybasic acid or derivative thereof, a polyol and a fatty acid, the liquid polymer having a melting point less than about 40° C., as determined by differential scanning calorimetry.

40 Claims, No Drawings

OTHER PUBLICATIONS

U.S. Appl. No. 10/323,367, A. Nathan.
U.S. Appl. No. 10/322,154, A. Nathan.
U.S. Appl. No. 10/322,117, A. Nathan.
U.S. Appl. No. 10/112,201, Nathan et al.
EPO Search Report dated Dec. 15, 2003 for EPO Appl. No. EP 03 25 1999.
Database WPI Week 199430 Derwent Publications Ltd., London, GB; an 1994-248859 XP002256761 & WO 94 15591 A. (Hisamitsu), Jul. 12, 1994 abstract.
Mark H.F.: "Alkyd Resins", Encyclopedia of Polmer Sience and Engineering. A to Amorphous Polymers, New York, J. Wiley & Sons, US. vol. 1, pp. 644-648 xP002035651 *the whole document*.
Emiko Koyama, Fumio Sanda, and Takeshi Endo, "Synthesis of Poly(ester-amide)s Derived from Optically Active Amino Alcohols," Macromol. Symp., 122, 275-280 (1997).
Emiko Koyama, Fumio Sanda, and Takeshi Endo, "Polycondensations of Hydroxycarboxylic Acids Derived from Optically Active Amioalcohols and Acid Anhydrides—Syntheses of Functional Poly(ester-amide)s," Journal of Polymer Science: Part A: Polymer Chemistry 35, 345-352 (1997).
Donald L. Elbert, Alison B. Pratt, Matthias P. Lutolf, Sven Halstenberg, Jeffrey A. Hubbell, "Protein Delivery from Materials Formed by Self-selective Conjugate Addition Reactions," Journal of Controlled Release, 76, 11-25 (2001).
Brian Parkyn F. Lamb and B. V. Clifton, "Polyesters Volume 2 Unsaturated Polyesters and Polyester Plasticisers," London Cliffe Books Ltd., New York American Elsevier ublishing Company, Inc., 1967 pp. 107-122.
Temple C. Patton, "Alkyd Resin Technology—Formulating Techniques and Allied Calculations," Interscience Publishers, a of John Wiley and Sons, New York—London 1962, pp. 13-31.

* cited by examiner

BONE REPLACEMENT MATERIALS UTILIZING BIOABSORBABLE LIQUID POLYMERS

FIELD OF THE INVENTION

The present invention relates to bone replacement devices and materials that utilize bioabsorbable and biocompatible polymeric liquids.

BACKGROUND OF THE INVENTION

Both natural and synthetic polymers, including homopolymers and copolymers, which are both biocompatible and absorbable in vivo are known for use in the manufacture of medical devices that are implanted in body tissue and absorb over time. Examples of such medical devices include suture anchor devices, sutures, staples, surgical tacks, clips, plates and screws, drug delivery devices, adhesion prevention films and foams, and tissue adhesives.

Natural polymers may include catgut, cellulose derivatives and collagen. Natural polymers typically absorb by an enzymatic degradation process in the body.

Synthetic polymers may include aliphatic polyesters, polyanhydrides and poly(orthoester)s. Synthetic absorbable polymers typically degrade by a hydrolytic mechanism. Such synthetic absorbable polymers include homopolymers, such as poly(glycolide), poly(lactide), poly($\epsilon$-caprolactone), poly(trimethylene carbonate) and poly(p-dioxanone), and copolymers, such as poly(lactide-co-glycolide), poly(s-caprolactone-coglycolide), and poly(glycolide-co-trimethylene carbonate). The polymers may be statistically random copolymers, segmented copolymers, block copolymers or graft copolymers.

Several injectable, bioabsorbable liquid copolymers suitable for use in parenteral applications as well as hard and soft tissue repair or augmentation materials in animals have been described. These liquid polymers contain lactone repeating units, including $\epsilon$-caprolactone trimethylene carbonate, ether lactone, glycolide, lactide, p-dioxanone, and combinations thereof. These liquid copolymers, however, are slow to degrade, taking over six months to be absorbed by the body.

Alkyd-type polyesters prepared by the polycondensation of a polyol, polyacid and fatty acid are used in the coating industry in a variety of products, including chemical resins, enamels, varnishes and paints. These polyesters also are used in the food industry to make texturized oils and emulsions for use as fat substitutes.

There is a great need for polymers for use in drug delivery and medical devices that permit solvent-free processing techniques in preparation of medical devices and compositions and that biodegrade within 6 months.

SUMMARY OF THE INVENTION

The present invention is directed to bone replacement devices and compositions comprising a synthetic, bioabsorbable, biocompatible liquid polymer comprising the reaction product of a polybasic acid or derivative thereof, a fatty acid and a polyol, the liquid polymer having a melting point less than about 40° C., as determined by differential scanning calorimetry.

DETAILED DESCRIPTION OF THE INVENTION

Alkyd polymers have been prepared by several known methods. For example, alkyd-type polymers were prepared by Van Bemmelen (*J. Prakt. Chem.*, 69 (1856) 84) by condensing succinic anhydride with glycerol. In the "Fatty Acid" method (see Parkyn, et al. *Polyesters* (1967), Iliffe Books, London, Vol. 2 and Patton, In: *Alkyd Resins Technology*, Wiley-Interscience New York (1962)), a fatty acid, a polyol and an anhydride are mixed together and allowed to react. The "Fatty Acid-Monoglyceride" method includes a first step of esterifying the fatty acid with glycerol and, when the first reaction is complete, adding an acid anhydride. The reaction mixture then is heated and the polymerization reaction takes place. In the "Oil-Monoglyceride" method, an oil is reacted with glycerol to form a mixture of mono-, di-, and triglycerides. This mixture then is polymerized by reacting with an acid anhydride.

The synthetic, bioabsorbable, biocompatible liquid polymers utilized in the present invention are the reaction product of a polybasic acid or derivative thereof, a fatty acid, and a polyol, and may be classified as alkyd polyester liquids. Preferably, the liquid polymers of the present invention are prepared by the polycondensation of a polybasic acid or derivative thereof and a monoglyceride, wherein the monoglyceride comprises reactive hydroxy groups and fatty acid groups. The expected hydrolysis byproducts are glycerol, dicarboxylic acid(s), and fatty acid(s), all of which are biocompatible. Preferably, the liquid polymers utilized in the present invention will have a weight average molecular weight between about 1,000 daltons and about 100,000 daltons, as determined by gel permeation chromatography. The liquid polymers comprise an aliphatic polyester backbone with pendant fatty acid ester groups that exhibit relatively low melting points, e.g. less than about 40° C., preferably less than about 25° C.

Fatty acids used to prepare liquid polymers utilized in the present invention may be saturated or unsaturated, and may vary in length from $C_4$ to $C_{12}$ for saturated fatty acids, and $C_4$ to $C_{22}$ for unsaturated fatty acids. Examples of such fatty acids include, without limitation, stearic acid, palmitic acid, myrisitic acid, caproic acid, decanoic acid, lauric acid, linoleic acid and oleic acid.

Polyols that can be used to prepare the liquid polymers include, without limitation, glycols, polyglycerols, polyglycerol esters, glycerol, sugars and sugar alcohols. Glycerol is a preferred polyhydric alcohol due to its abundance and cost.

Monoglycerides which may be used to prepare liquid polymers utilized in the present invention include, without limitation, monostearoyl glycerol, monopalmitoyl glycerol, monomyrisitoyl glycerol, monocaproyl glycerol, monodecanoyl glycerol, monolauroyl glycerol, monolinoleoyl glycerol, monooleoyl glycerol, and combinations thereof. Preferred monoglycerides include monocaproyl glycerol, monodecanoyl glycerol, monolauroyl glycerol, monolinoleoyl glycerol, and monooleoyl glycerol.

Polybasic acids that can be used include natural multifunctional carboxylic acids, such as succinic, glutaric, adipic, pimelic, suberic, and sebacic acids; hydroxy acids, such as diglycolic, malic, tartaric and citric acids; and unsaturated acids, such as fumaric and maleic acids. Polybasic acid derivatives include anhydrides, such as succinic anhydride, diglycolic anhydride, glutaric anhydride and maleic anhydride, mixed anhydrides, esters, activated esters and acid halides. The multifunctional carboxylic acids listed above are preferred.

In certain embodiments of the invention, the liquid polymer may be prepared from the polybasic acid or derivative thereof, the monoglyceride and, additionally, at least on additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

In preparing the liquid polymers utilized in the present invention, the particular chemical and physical properties required of the liquid polymer for a particular use must be considered. For example, changing the chemical composition can vary the physical properties, including absorption times. Copolymers can be prepared by using mixtures of diols, triol, polyols, diacids, triacids, and different monoalkanoyl glycerides to match a desired set of properties. Similarly, blends of two or more alkyd polyesters may be prepared to tailor properties for different applications.

Alkyd polyester liquids of the present invention can be made more hydrophobic by increasing the length of the fatty acid side chain or the length of the diacid in the backbone, or by incorporating a long chain diol. Alternatively, alkyd polyester liquids of the present invention can be made more hydrophilic or amphiphilic by employing hydroxy acids, such as malic, tartaric and citric acids, or some oxadiacids, in the composition, or by employing poly(ethylene glycol)s or copolymers of polyethylene glycol and polypropylene glycol, commonly known as Pluronics, in the formation of segmented block copolymers.

Copolymers containing other linkages in addition to an ester linkage also may be synthesized; for example, ester-amides, ester-carbonates, ester-anhydrides and ester urethanes, to name a few.

Functionalized liquid polymers can be prepared by appropriate choice of monomers. Polymers having pendant hydroxyls can be synthesized using a hydroxy acid such as malic or tartaric acid in the synthesis. Polymers with pendent amines, carboxyls or other functional groups also may be synthesized. A variety of biologically active substances, hereinafter referred to as bioactive agents, can be covalently attached to these functional liquid polymers by known coupling chemistry to give sustained release of the bioactive agent. As used herein, bioactive agent is meant to include those substances or materials that have a therapeutic effect on mammals, e.g. pharmaceutical compounds.

In another embodiment, the polymers of the present invention may be endcapped in a variety of ways to obtain the desired properties. Endcapping reactions convert the terminal and pendant hydroxyl groups and terminal carboxyl groups into other types of chemical moieties. Typical endcapping reactions include but are not limited to alkylation and acylation reactions using common reagents such as alkyl, alkenyl, or alkynyl halides and sulfonates, acid chlorides, anhydrides, mixed anhydrides, alkyl and aryl isocyanantes and alkyl and aryl isothiocyantes. Endcapping reactions can impart new functionality to the polymers of this invention. For instance, when acryloyl or methacryloyl chloride is used to endcap these polymers, acrylate or methacrylate ester groups, respectively, are created that can subsequently be polymerized to form a crosslinked network.

One skilled in the art, once having the benefit of the disclosure herein, will be able to ascertain particular properties of the liquid polymers required for particular purposes, and readily prepare liquid polymers that provide such properties.

The polymerization of the alkyd polyester liquids preferably is performed under melt polycondensation conditions in the presence of an organometallic catalyst at elevated temperatures. The organometallic catalyst preferably is a tin-based catalyst e.g. stannous octoate. The catalyst preferably will be present in the mixture at a molar ratio of polyol and polycarboxylic acid to catalyst in the range of from about 15,000/1 to 80,000/1. The reaction preferably is performed at a temperature no less than about 120° C. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and melting temperature of the polymer. The preferred reaction conditions of temperature, time and pressure can be readily determined by assessing these and other factors.

Generally, the reaction mixture will be maintained at about 180° C. The polymerization reaction can be allowed to proceed at this temperature until the desired molecular weight and percent conversion is achieved for the copolymer, which typically will take from about 15 minutes to 24 hours. Increasing the reaction temperature generally decreases the reaction time needed to achieve a particular molecular weight.

In another embodiment, copolymers of alkyd polyester liquids can be prepared by forming an alkyd polyester prepolymer polymerized under melt polycondensation conditions, then adding at least one lactone monomer or lactone prepolymer. The mixture then would be subjected to the desired conditions of temperature and time to copolymerize the prepolymer with the lactone monomers.

The molecular weight of the prepolymer, as well as its composition, can be varied depending on the desired characteristic that the prepolymer is to impart to the copolymer. Those skilled in the art will recognize that the alkyd polyester prepolymers described herein can also be made from mixtures of more than one diol or dioxycarboxylic acid.

One of the beneficial properties of the alkyd polyester liquids of this invention is that the ester linkages are hydrolytically unstable, and therefore the polymer is bioabsorbable because it readily breaks down into small segments when exposed to moist body tissue. In this regard, while it is envisioned that co-reactants could be incorporated into the reaction mixture of the polybasic acid and the diol for the formation of the alkyd polyester, it is preferable that the reaction mixture does not contain a concentration of any co-reactant which would render the subsequently prepared polymer nonabsorbable. Preferably, the reaction mixture is substantially free of any such co-reactants if the resulting polymer is rendered nonabsorbable.

In one embodiment of the invention, the alkyd polyester liquids of the present invention can be used as a pharmaceutical carrier in a drug delivery matrix, or as a cell-based carrier in a tissue engineering application. To form the matrix, the liquid polymer would be mixed with an effective amount of a bioactive agent to form the matrix. The variety of bioactive agents that can be used in conjunction with the liquid polymer of the invention is vast. In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppresives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics.

Rapamycin, risperidone, and erythropoietin are several bioactive agents that may be used in drug delivery matrices of the present invention.

In two particularly preferred embodiments the bioactive agents for administration in conjunction with the bioerodible polymers of the invention are antibacterial agents for the treatment of deep wounds, and antibiotics for periodontal treatment (e.g., tetracycline or the like). Other preferred drugs for use with the presently disclosed polymers include proteinaceous drugs such as growth factors or growth hormones.

The drug delivery matrix may be administered in any suitable dosage form such as parenterals, bioerodible ointments, gels, creams, and similar soft dosage forms adapted for the parenteral or topical administration of bioactive agents. Other modes of administration (e.g., transdermal) and compositional forms (e.g., more rigid transdermal forms) are within the scope of the invention as well.

Parenteral administration of a bioerodible composition of the invention can be effected by either subcutaneous, or intramuscular injection. Parenteral formulations of the copolymer may be formulated by mixing one or more pharmaceuticals with a liquid copolymer. Other suitable parenteral additives may be formulated with the copolymer and pharmaceutical active. However, if water is to be used it should be added immediately before administration. The bioerodible ointment, gel or cream may also be injected as is or in combination with one or more suitable auxiliary components as described below. Parenteral delivery is preferred for administration of proteinaceous drugs such as growth factors, growth hormone, or the like.

The bioerodible ointments, gels and creams of the invention will include an ointment, gel or cream base comprising one or more of the copolymers described herein and a selected bioactive agent. The bioactive agent, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The quantity and type of copolymers incorporated into the parenteral, ointment, gel, cream, etc., is variable. For a more viscous composition, a higher molecular weight polymer is used. If a less viscous composition is desired, a lower molecular weight polymer can be employed. The product may contain blends of the liquid or low melting point copolymers to provide the desired release profile or consistency to a given formulation.

While not essential for topical or transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N,N-dimethylacetamide (DMA), deslymethylsulfoxide, ethanol, eucalyptol, lecithin, and the 1-N-dodecylcyclazacycloheptan-2-ones.

Depending on dosage form, the pharmaceutical compositions of the present invention may be administered in different ways, i.e., parenterally, topically, or the like. Preferred dosage forms are liquid dosage forms that can be administered parenterally.

The amount of bioactive agent will be dependent upon the particular drug employed and medical condition being treated. Typically, the amount of drug represents about 0.001% to about 70%, more typically about 0.001% to about 50%, most typically about 0.001% to about 20% by weight of the matrix.

The quantity and type of alkyd polyester liquid incorporated into the parenteral, ointment, gel or cream will vary depending on the release profile desired and the amount of drug employed. The product may contain blends of polyesters to provide the desired release profile or consistency to a given formulation.

The alkyd polyester liquid, upon contact with body fluids including blood or the like, undergoes gradual degradation, mainly through hydrolysis, with concomitant release of the dispersed drug for a sustained or extended period, as compared to the release from an isotonic saline solution. This can result in prolonged delivery, e.g. over about 1 to about 2,000 hours, preferably about 2 to about 800 hours) of effective amounts, e.g. 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drugs and alkyd polyester liquid may be tested in appropriate in vitro and in vivo models to achieve the desired drug release profiles. For example, a drug could be formulated with an alkyd polyester liquid and parenterally administered to an animal. The drug release profile could then be monitored by appropriate means, such as by taking blood samples at specific times and assaying the samples for drug concentration. Following this or similar procedures, those skilled in the art will be able to formulate a variety of formulations.

In a further embodiment of the present invention the injectable liquid polymers can be used for a variety of soft tissue repair and augmentation procedures. For example, the liquid polymers can be used in facial tissue repair or augmentation including but not limited to camouflaging scars, filling depressions, smoothing out irregularity, correcting asymmetry in facial hemiatrophy, second branchial arch syndrome, facial lipodystrophy and camouflaging age-related wrinkles as well as augmenting facial eminences (lips, brow, etc.). Additionally, these injectable liquid polymers can be used to restore or improve sphincter function such as for treating stress urinary incontinence. Other uses of these injectable liquid polymers may also include the treatment of vesicoureteral reflux (incomplete function of the inlet of the ureter in children) by subureteric injection and the application of these liquid polymers as general purpose fillers in the human body.

Surgical applications for injectable, biodegradable liquid polymers include, but are not limited to, facial contouring (frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like); periurethral injection including injection into the submucosa of the urethra along the urethra, at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic affect. Surgical specialists who would use such a product include, but are not limited to, plastic and reconstructive surgeons, dermatologists, facial plastic surgeons, cosmetic surgeons, otolaryngologists, urologists, gynecologists, gastroenterologists, ophthalmologists and any other physician qualified to utilize such a product.

The liquid copolymers can be administered with a syringe and needle or a variety of devices. It is also envisioned that the liquid polymers could be sold in the form of a kit comprising a device containing the liquid polymers. The device having an outlet for said liquid polymers, an ejector for expelling the liquid polymers and a hollow tubular member fitted to the outlet for administering the liquid polymers into an animal.

Additionally, the liquid polymers, when sterilized, are useful as adhesion prevention barriers.

In another embodiment, the liquid polymer is used to coat a surface of a surgical article to enhance the lubricity of the coated surface. The polymer may be applied as a coating using conventional techniques.

It is contemplated that numerous surgical articles, including but not limited to sutures, needles, orthopedic pins, clamps, screws, plates, clips, e.g. for vena cava, staples, hooks, buttons, snaps, bone substitutes, e.g. as mandible prosthesis, intrauterine devices, e.g. as spermicidal devices, draining or testing tubes or capillaries, surgical instruments, vascular implants or supports, e.g. stents or grafts, or combinations thereof, vertebral discs, extracorporeal tubing for kidney and heart-lung machines, artificial skin, and supports for cells in tissue engineering applications, can be coated with the liquid polymers of this invention to improve the surface properties of the article.

In yet another embodiment, the medical device comprises a bone replacement material comprising the liquid polymer. The bone replacement materials may further comprise liquid polymer mixed with a bioactive agent in a therapeutically effective amount, such a growth factor, to facilitate growth of bone tissue. Examples of bioactive agents suitable for use with the present invention include cell attachment mediators, such as peptide-containing variations of the "RGD" integrin binding sequence known to affect cellular attachment, biologically active ligands, and substances that enhance or exclude particular varieties of cellular or tissue ingrowth. Examples of such substances include integrin binding sequence, ligands, bone morphogenic proteins, epidermal growth factor, IGF-I, IGF-II, TGF-β I–III, growth differentiation factor, parathyroid hormone, vascular endothelial growth factor, hyaluronic acid, glycoprotein, lipoprotein, bFGF, TGF$_\beta$ superfamily factors, BMP-2, BMP-4, BMP-6, BMP-12, sonic hedgehog, GDF5, GDF6, GDF8, PDGF, small molecules that affect the upregulation of specific growth factors, tenascin-C, fibronectin, thromboelastin, thrombin-derived peptides, heparin-binding domains, and the like. Furthermore, the bone replacement material may comprise liquid polymer mixed with a biologically derived substance selected from the group consisting of demineralized bone matrix (DBM), platelet rich plasma, bone marrow aspirate and bone fragments, all of which may be from autogenic, allogenic, or xenogenic sources.

Alternatively, the bone replacement material may comprise liquid polymer mixed with an inorganic filler. The inorganic filler may be selected from alphatricalcium phosphate, beta-tricalcium phosphate, calcium carbonate, barium carbonate, calcium sulfate, barium sulfate, hydroxyapatite, and mixtures thereof. In certain embodiments the inorganic filler comprises a polymorph of calcium phosphate. Preferably, the inorganic filler is hydroxyapatite.

The bone replacement materials may still further comprise liquid polymer mixed with a bioactive agent in a therapeutically effective amount and an inorganic filler.

In still yet another embodiment, the bone replacement material may comprise liquid polymer mixed with appropriate cell types prior to implantation. Cells which can be seeded or cultured in the liquid polymers of the current invention include, but are not limited to, bone marrow cells, mesenchymal cells, stromal cells, stem cells, embryonic stem cells, osteoblasts, precursor cells derived from adipose tissue, bone marrow derived progenitor cells, peripheral blood progenitor cells, stem cells isolated from adult tissue, and genetically transformed cells, or combinations of the above.

The bone replacement liquid polymers of the present invention may be used in applications such as the filling of trauma defects. Alternatively, they may be coated on orthopaedic devices to facilitate bone regeneration. Such devices include, but are not limited to plates, nails, screws, rods, and suture anchors.

Furthermore, the bone replacement liquid polymers may be injected into, or coated on, naturally or synthetically derived tissue engineering scaffolds and spinal cages. Naturally derived tissue engineering scaffolds include those formed from small intestinal submucosa, collagen, hyaluronic acid, chitosan, and alginates. These scaffolds may be in the form of porous materials such as foams or sponges, or in fibrous form, such as weaves, braids, or nonwovens.

The relative amounts of liquid polymer, bioactive agent, cells, and inorganic filler may be determined readily by one skilled in the art by routine experimentation after having the benefit of this disclosure.

The examples set forth below are for illustration purposes only, and are not intended to limit the scope of the claimed invention in any way. Numerous additional embodiments within the scope and spirit of the invention will become readily apparent to those skilled in the art.

In the examples below, the synthesized polymeric waxes were characterized via differential scanning calorimetry (DSC), gel permeation chromatography (GPC), and nuclear magnetic resonance (NMR) spectroscopy. DSC measurements were performed on a 2920 Modulated Differential Scanning Calorimeter from TA Instruments using aluminum sample pans and sample weights of 5–10 mg. Samples were heated from room temperature to 100° C. at 10° C./minute; quenched to −40° C. at 30° C./minute followed by heating to 100° C. at 10° C./minute. For GPC, a Waters System with Millennium 32 Software and a 410 Refractive Index Detector were used. Molecular weights were determined relative to polystyrene standards using THF as the solvent. Proton NMR was obtained in deuterated chloroform on a 400 MHz NMR spectrometer using Varian software.

EXAMPLE 1

Synthesis of Poly(glyceryl monolinoleate-succinate)

29.97 gm (84.6 mmoles) of glyceryl monolinoleate were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 8.47 gm (84.6 mmoles) succinic anhydride were added and the temperature was raised to 200° C. Heat tape was wrapped around the outside of the top of the flask and adapter to keep the succinic anhydride from subliming. The reaction was continued for 3 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 mls EtOAc) and added to a separatory funnel. The solution was washed three times with 20 mls of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated to give a viscous yellow liquid. The polymer was dried in the vacuum oven, where the oven was set around 40° C., for 48–72 hours.

GPC measurement determined a number average molecular weight of 2,264, and a weight average molecular weight of 3,955 daltons.

EXAMPLE 2

Synthesis of Poly(glyceryl monolinoleate-succinate)

The same procedure as Example 1 was used, except the reaction was maintained at 200° C. for 24 hours.

GPC measurement determined a number average molecular weight of 6,624, and a weight average molecular weight of 83,214 daltons.

EXAMPLE 3

Synthesis of Poly(glyceryl monooleate-succinate)

30.0 gm (84.1 mmoles) of glyceryl monooleate were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 8.42 gm (84.1 mmoles) succinic anhydride was added and the temperature was raised to 200° C. Heat tape was wrapped around the outside of the top of the flask and adapter to keep the succinic anhydride from subliming. The reaction was continued for 3 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 mls EtOAc) and added to a separatory funnel. The solution was washed three times with 20 mls of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated to give a viscous yellow liquid. The polymer was dried in the vacuum oven, where the oven was set around 40° C., for 48–72 hours.

GPC measurement determined a number average molecular weight of 2,145, and a weight average molecular weight of 3,659 daltons.

EXAMPLE 4

Synthesis of Poly(glyceryl monooleate-succinate)

The same procedure as Example 3 was used, except the reaction was maintained at 200° C. for 24 hours.

GPC measurement determined a number average molecular weight of 3,246, and a weight average molecular weight of 29,303.

EXAMPLE 5

Synthesis of 50:50 Poly(monostearoyl glycerol-co-glyceryl monolinoleate-succinate)

25.0 gm (70.5 mmoles) of glyceryl monolinoleate and 25.3 gm (70.5 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 14.1 gm (141.0 mmoles) succinic anhydride were added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer crystallized to an off white pasty solid.

DSC measurements found a melting point of 32.49° C., and a specific heat of 33.33 J/g. GPC measurement determined a number average molecular weight of 2,500, and a weight average molecular weight of 3,964.

EXAMPLE 6

Synthesis of 50:50 Poly(monostearoyl glycerol-co-glyceryl monooleate-succinate)

25.0 gm (70.1 mmoles) of glyceryl monooleate and 25.2 gm (70.1 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 14.0 gm (140.2 mmoles) succinic anhydride were added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer crystallized to an off-white pasty solid.

DSC measurements found a melting point of 29.31° C., and a specific heat of 32.43 J/g. GPC measurement determined a number average molecular weight of 2,406, and a weight average molecular weight of 3,739 daltons.

EXAMPLE 7

Synthesis of 25:75 Poly(monostearoyl glycerol-co-glyceryl monolinoleate-succinate)

37.49 gm (105.8 mmoles) of glyceryl monolinoleate and 12.64 gm (35.3 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 14.1 gm (141.0 mmoles) succinic anhydride were added and the temperature was raised to 200° C. Heat tape was wrapped around the outside of the top of the flask and adapter to keep the succinic anhydride from subliming. The reaction was continued for 3.0 hours at 200° C. The flask was removed from the oil bath and allowed to cool to room temperature. The polymer was a very viscous, light amber liquid.

For purification, the polymer was dissolved in Ethyl acetate (5.0 gm polymer in 20 mls EtOAc) and added to a separatory funnel. The solution was washed three times with 20 mls of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate. The solution was gravity filtered and evaporated down to give a viscous yellow liquid. The polymer was dried in the vacuum oven, where the oven was set around 40° C., for 48–72 hours.

DSC measurements found a melting point of about 20° C. GPC measurement determined a number average molecular weight of 2,115, and a weight average molecular weight of 3,326 daltons.

EXAMPLE 8

Synthesis of 25:75 Poly(monostearoyl glycerol-co-glyceryl monooleate-succinate)

44.12 gm (123.8 mmoles) of glyceryl monooleate and 14.79 gm (41.3 mmoles) of monostearoyl glycerol were added to a dry 100 ml, single neck, round bottom flask. A football stir bar was added and a nitrogen inlet adapter was attached. The reaction flask was placed into a room temperature oil bath and a nitrogen blanket was applied. The oil bath temperature was raised to 140° C. Once at 140° C., 16.51 gm (165.0 mmoles) succinic anhydride was added and the temperature was raised to 200° C. Heat tape was wrapped around the outside of the top of the flask and adapter to keep the succinic anhydride from subliming. The reaction was allowed to cook for 3.0 hours at 200° C. The flask was removed from the oil bath and allowed to cool to room temperature. The polymer was a pale yellow, viscous liquid.

For purification, the polymer was dissolved in Ethyl acetate (5.0 gm polymer in 20 mls EtOAc) and added to a separatory funnel. The solution was washed three times with 20 mls of a very dilute sodium bicarbonate solution. The funnel was agitated very slightly (in order to avoid forming an emulsion). The solution was then washed three times with a saturated sodium chloride solution. The polymer solution was decanted and dried over magnesium sulfate for approximately one hour. The solution was gravity filtered and rotovapped down to give a viscous yellow liquid. The polymer was dried in the vacuum oven, where the oven was set around 40° C., for 48–72 hours. An $^1$H NMR was taken to make sure all of the solvent was removed.

DSC measurements found a melting point of 18.18° C., and a specific heat of 18.29 J/g. GPC measurement determined a number average molecular weight of 1,933, and a weight average molecular weight of 7,122 daltons.

EXAMPLE 9

Synthesis of Poly(monodecanoyl glycerol-co-succinate)

15.0 gm (60.9 mmoles) monodecanoyl-rac-glycerol were added to a dry 50 ml, single neck, round bottom flask. A teflon football stirbar was added and a nitrogen inlet adapter was attached. The reaction flask was placed in a room temperature oil bath and a nitrogen gas blanket was started. The reaction temperature was increased to 140° C. Once at 140° C., 6.09 gm (60.9 mmoles) of succinic anhydride was added. The temperature was raised to 200° C. and maintained at this temperature for three hours. The reaction was removed from the oil bath and allowed to cool to room temperature. The polymer was a light amber liquid. Crystallites began to form within ten days.

GPC measurement determined a number average molecular weight of 1,460, and a weight average molecular weight of 3,929 daltons. The $^1$H NMR showed the following peaks: δ 0.86 triplet (3H), 1.34 multiplet (12H), 1.62 multiplet (2H), 2.32 multiplet (2H), 2.72 multiplet (2H), 4.15 multiplet (2H), 4.35 multiplet (2H), 5.29 multiplet (1H).

EXAMPLE 10

Synthesis of Poly(monolauroyl-rac-glycerol-co-succinate)

14.0 gm (50 mmoles) monolauroyl glycerol were added to a dry 50 ml, single neck, round bottom flask. A stir bar was added and a nitrogen inlet adapter was attached. The reaction flask was placed in a room temperature oil bath and a nitrogen gas blanket was applied. The flask was heated to 140° C. Once at 140° C., 5.0 gm (50 mmoles) of succinic anhydride were added. The temperature was raised to 200° C. and maintained at this temperature for 3 hours. After 3 hours the reaction flask was removed from the oil bath and allowed to cool to room temperature. The polymer was a dark yellow liquid. Crystallites began to form within seven days.

GPC measurement determined a number average molecular weight of 1,284, and a weight average molecular weight of 2,198. The $^1$H NMR showed the following peaks: δ 0.85 triplet (3H), 1.17 multiplet (16H), 1.6 multiplet (2H), 2.29 multiplet (2H), 2.6 multiplet (4H), 4.23 multiplet (4H), 5.27 multiplet (2H).

EXAMPLE 11

Synthesis of Poly(monocaproyl glycerol-co-succinate)

15.0 gm (68.7 mmoles) monocapryloyl glycerol were added to a dry 50 ml, single neck, round bottom flask. A stir bar was added and a nitrogen inlet adapter was attached. The reaction flask was placed in a room temperature oil bath and a nitrogen blanket was applied. The flask was heated to 140° C. and then 6.88 gm (68.7 mmoles) of succinic anhydride were added. The temperature was raised to 200° C. and the solution was held at this temperature for 3 hours. After 3 hours the flask was removed from the oil bath and allowed to cool to room temperature. The polymer was a light yellow viscous liquid. The polymer began to crystallize very slowly in 7–10 days.

GPC measurement determined a number average molecular weight of 1,349, and a weight average molecular weight of 2,301 daltons. The $^1$H NMR showed the following peaks: δ 0.86 triplet (3H), 1.25 multiplet (8H), 1.6 multiplet (2H), 2.30 multiplet (2H), 2.65 multiplet (4H), 4.13 multiplet (2H), 4.33 multiplet (2H), 5.26 multiplet (1H).

EXAMPLE 12

Synthesis of Poly(monostearoyl glycerol-co-succinate) room temperature solid 8.0 gm (22.3 mmoles) of monostearoyl glycerol were added to a dry 50 mL, single neck, round bottom flask. A stir bar was added and a nitrogen inlet adapter was attached. The reaction flask was placed in a room temperature oil bath and a nitrogen gas blanket was started. The flask was heated to 140° C. and 4.46 gm (44.6 mmoles) of succinic anhydride were added. The temperature was raised to 200° C. and maintained for 22.5 hours. The flask was removed from the oil bath to cool to room temperature. Once the solution crystallized, it was deglassed and cleaned of any glass fragments. The polymer was an amber colored solid.

DSC measurements found a melt temperature of 48.41° C. and a specific heat of 73.98 J/g. GPC measurement determined a number average molecular weight of 2,546, and a weight average molecular weight of 43,002 daltons.

EXAMPLE 13

Poly(monostearoyl glycerol-co-glyceryl monolinoleate-succinate) liquid polymer as a bone replacement material A bone replacement study was performed in male New Zealand white rabbits using poly(monostearoyl glycerol-co-glyceryl monolinoleate-succinate) liquid. The animals utilized in this study were handled and maintained in accordance with current requirements of the Animal Welfare Act. Compliance with the above Public Laws was accomplished by adhering to the Animal Welfare regulations (9 CFR) and conforming to the current standards promulgated in the Guide for the Care and Use of Laboratory Animals.

Liquid poly(monostearoyl glycerol-co-glyceryl monolinoleate-succinate) was prepared as described in Example 7. The polymer was heat sterilized in glass vials sealed with a crimped aluminum seal and a septum. The vials were heated to 160° C. in an oven for 2 hours. The outside of the vials were then cleaned using a 70/30 mix of isopropanol and deionized water before the vial was introduced into a sterile, laminar flow hood. The polymer was then loaded into 3 cc sterile syringes in a sterile hood and injected into the radial defect (2– 2.5 cm) of four rabbits until the defect was filled. Explants were taken at 8 weeks.

In two of the four defects, bone regeneration or bone bridging was observed. Radiographic data showed gradual healing of the defect in these two cases. In the case that resulted in bone bridging, this result appeared to be fully achieved within four weeks. By eight weeks, the bone appeared to be re-corticalized which was confirmed by gross histology.

EXAMPLE 14

Poly(monostearoyl glycerol-co-glyceryl monolinoleate-succinate) liquid polymer mixed with demineralized bone matrix (DBM) as a bone replacement material A bone replacement study was performed in male New Zealand white rabbits using a mixture of poly(monostearoyl glycerol-co-glyceryl monolinoleatesuccinate) liquid polymer and demineralized bone matrix (DBM). The animals utilized in this study were handled and maintained in accordance with current requirements of the Animal Welfare Act. Compliance with the above Public Laws was accomplished by adhering to the Animal Welfare regulations (9 CFR) and conforming to the current standards promulgated in the Guide for the Care and Use of Laboratory Animals.

Liquid poly(monostearoyl glycerol-co-glyceryl monolinoleate-succinate) was prepared as described in Example 7. The polymer was heat sterilized in glass vials sealed with a crimped aluminum seal and a septum. The vials were heated to 160° C. in an oven for 2 hours. The outside of the vials were then cleaned using a 70/30 mix of isopropanol and deionized water before the vial was introduced into a sterile, laminar flow hood. Also loaded into the sterile hood were 2, 1 cc packets of rabbit DBM prepared by VTS Inc. (Kent, Wash.). The liquid polymer was mixed with DBM in a sterile petri dish with the aid of a stainless steel spatula at a DBM to polymer carrier ratio of 2:1 ratio forming a paste-like formulation of 67 weight percent DBM. The formulation was then loaded into sterile syringes with cut ends. The filling volume was 0.5 cc and each syringe was packaged in a pre-autoclaved sterile pouch before removal from the sterile hood.

The surgical procedure for implantation of these samples into defects in the radii of 5 rabbits is as follows. A longitudinal skin incision was made over the middle one third of the right front leg. The periosteum was then separated from the muscle and a 17 mm osteo-periosteal defect was made in the radius. The radial segment was cut using an air powered mini driver equipped with an oscillating saw attachment. The defect was located approximately 2.0 to 2.5 cm proximal to the radiocarpal joint. No additional fixation or hardware was necessary to stabilize the limb due to the strutting of the forelimb by the ulna. The samples were implanted by injecting the polymer into the radial defect from the above prepared syringes until the defect was filled (~0.3 cc). All incisions were closed with multiple layers of resorbable suture upon completion of the operation.

Radiographic data was taken every two weeks to monitor the implant site. Explants were taken at 8 weeks and in all 5 cases bone bridging occurred. The defect sites in three of the five cases were sunken and in general, the sites reflected a diffuse pattern with no organized structure. As early as 2 weeks, the defect site was cloudy, emphasizing the osteoinductivity of the DBM.

EXAMPLE 15

25:75 Poly(monostearoyl glycerol-co-glyceryl monooleate-succinate) liquid polymer mixed with demineralized bone matrix (DBM) as a bone replacement material A bone replacement study was performed in male New Zealand white rabbits using a mixture of 25:75 poly (monostearoyl glycerol-co-glyceryl monooleate-succinate) liquid polymer and demineralized bone matrix (DBM).

Liquid 25:75 poly(monostearoyl glycerol-co-glyceryl monooleate-succinate) was prepared as described in Example 8. The polymer was heat sterilized, mixed with DBM and implanted into defects made in the radii of 5 rabbits following the procedure used in Example 14.

Radiographic data was taken every two weeks to monitor the implant site. Explants were taken at 8 weeks and in all 5 cases, bone bridging occurred. As in Example 14, some of the defect sites had a sunken appearance but, in general, the radiographic data indicated a slightly more organized cancellous appearance to the newly formed bone. At 2 weeks, the defect site was cloudy, emphasizing the osteoinductivity of the DBM.

EXAMPLE 16

Poly(glyceryl monooleate-succinate) liquid polymer mixed with demineralized bone matrix (DBM) as a bone replacement material A bone replacement study was performed in male New Zealand white rabbits using a mixture of poly(glyceryl monooleate-succinate) liquid polymer and demineralized bone matrix (DBM).

Liquid poly(glyceryl monooleate-succinate) was prepared as described in Example 3. The polymer was heat sterilized, mixed with DBM and implanted into defects made in the radii of 5 rabbits following the procedure used in Example 14.

Radiographic data was taken every two weeks to monitor the implant site. Explants were taken at 8 weeks and, in all 5 cases, bone bridging occurred. The observed healing was advanced in comparison to that observed in Examples 14 and 15. Three of the defect sites showed not only complete bridging, but also clear evidence of recorticalization. In one case, there was evidence of restoration of the marrow cavity. At 2 weeks, the defect site was cloudy, emphasizing the osteoinductivity of the DBM. The extent to which this cloudiness was visible was more prominent than in the other Examples 14 and 15.

EXAMPLE 17

Poly(glyceryl monooleate-succinate) liquid polymer end-capped with oleoyl chloride A polymer was prepared following the procedure in Example 3, except using 253.12 g (0.71 mol) of glycerol monooleate and 70.05 g (0.7 mol) of succinic anhydride in a 500 ml single neck, round bottom flask. GPC measurement determined a number average molecular weight of 2,280 and a weight average molecular weight of 4,040 daltons.

An end-capping procedure was performed by dissolving 25.2 g of the polymer in 75 ml of methylene chloride in a three necked, 300 ml, round bottom flask, to which 3.35 grams of triethyl amine was added as an acid scavenger. The flask was equipped with a glass stirrer with a teflon paddle, a thermometer, and a septum with $N_2$ inlet/outlet needles. The flask was placed in a ice/NaCl slush bath, and the reaction mixture was allowed to chill to 0° C. A nitrogen blanket was placed over the reaction through the septum.

In the glove box, 9.74 g oleoyl chloride was weighed in a gas-tight syringe, and the needle was stoppered using a rubber stopper. The oleoyl chloride was added to the chilled reaction mixture through the septum in a dropwise fashion so as to keep the reaction temperature between 2 and 7° C., as read on the thermometer. After complete addition of the oleoyl chloride, the reaction was allowed to continue stirring for another 2 hours. While still stirring, the slush bath was removed and the reaction mixture was allowed to come to room temperature at which point 2 ml of ethanol was added to the solution and let stir for 1 hour to react with any excess oleoyl chloride. The stirring was stopped, and the reaction was stoppered and allowed to sit in the refrigerator overnight.

The triethylamine hydrochloride salt was removed by vacuum filtration and the filtercake was washed twice with 25 ml of cold methylene chloride. The product-containing methylene chloride solution was transferred to a 500 ml separatory funnel and washed twice with equal volumes of 1.0 M HCL followed by two washings with equal volumes of brine solution. The organic layer was then dried over magnesium sulfate.

The magnesium sulfate was removed by vacuum filtration over Celite. Finally, the methylene chloride was removed by evaporation on a rotary evaporator leaving behind the end-capped polymer which was allowed to dry in a vacuum oven at room temperature until it exhibited constant weight.

$H^1$ NMR showed the following peaks: δ 0.84 triplet, 1.29 doublet, 1.63 multiplet, 2.01 multiplet, 2.30 multiplet, 2.45 triplet, 2.63 multiplet, 4.23 multiplet, and 5.34 multiplet. Following the end-capping reaction, the peaks assigned to the terminal hydroxyl endgroups at δ 3.5–3.8 on the starting polymer were not resolvable above the baseline, indicating that the terminal hydroxyl groups were converted into esters.

The polymer was heat sterilized for 2 hours at 160° C. and mixed with DBM following the procedure used in Example 14 in order to make a bone replacement material.

EXAMPLE 18

Poly(glyceryl monooleate-succinate) liquid polymer end-capped with acetyl chloride Poly(glyceryl monooleate-succinate) liquid polymer was prepared following the method of Example 17.

An end-capping procedure with 2.6 g acetyl chloride was performed using the same procedure as described in Example 17, except using 25.04 g of the polymer in methylene chloride, to which 3.35 grams of triethyl amine was added as an acid scavenger. The end-capped polymer product which was allowed to dry in a vacuum oven at 80° C. until it exhibited constant weight.

$H^1$ NMR showed the following peaks: δ 0.85 triplet, 1.30 doublet, 1.61 multiplet, 2.02 multiplet, 2.32 multiplet, 2.62 multiplet, 4.23 multiplet, and 5.33 multiplet. Following the end-capping reaction, the peaks assigned to the terminal hydroxyl endgroups at δ 3.5– 3.8 on the starting polymer were not resolvable above the baseline, indicating that the terminal hydroxyl groups were converted into esters.

EXAMPLE 19

End-capped Poly(monooleate-succinate) liquid polymer mixed with demineralized bone matrix (DBM) as a bone replacement material A bone replacement study was performed in male New Zealand white rabbits using a mixture of the end-capped liquid polymer as described in Example 18 and demineralized bone matrix (DBM).

The polymer was heat sterilized for 2 hours at 160° C. and mixed with DBM, and the sterile samples were implanted into defects made in the radii of 5 rabbits as in Example 14.

We claim:

1. A medical device, comprising: a bone replacement material, said bone replacement material comprising a synthetic, bioabsorbable, biocompatible liquid polymer comprising the reaction product of a polybasic acid or derivative thereof, a fatty acid, and a polyol, said liquid polymer comprising an aliphatic polyester backbone having fatty acid ester groups pending therefrom and said liquid polymer having a melting point less than about 40° C., as determined by differential scanning calorimetry wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters, and acid halides.

2. The medical device of claim 1 wherein said liquid polymer comprises the reaction product of said polybasic acid or derivative thereof and a monoglyceride, said monoglyceride comprising the reaction product of said fatty acid and said polyol.

3. The medical device of claim 2 wherein said polybasic acid or derivative thereof is selected from the group consisting of succinic acid, succinic anhydride, malic acid, tartaric acid, citric acid, diglycolic acid, diglycolic anhydride, glutaric acid, glutaric anhydride, adipic acid, pimelic acid, suberic acid, sebacic acid, fumaric acid, maleic acid, maleic anhydride, mixed anhydrides, esters, activated esters, and acid halides.

4. The medical device of claim 3 wherein said polybasic acid derivative is succinic anhydride.

5. The medical device of claim 3 wherein said polybasic acid is succinic acid.

6. The medical device of claim 1 wherein said liquid polymer comprises a liquid copolymer.

7. The medical device of claim 6 wherein said liquid copolymer comprises the reaction product of said fatty acid, said polyol, and at least two of said polybasic acids or derivatives thereof selected from the group consisting of succinic acid, succinic anhydride, malic acid, tartaric acid, citric acid, diglycolic acid and diglycolic anhydride.

8. The medical device of claim 6 wherein said liquid copolymer comprises the reaction product of said polybasic acid or derivative thereof, and at least two monoglycerides selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol.

9. The medical device of claim 6 wherein said liquid copolymer comprises the reaction product of said polybasic acid or derivative thereof, a monoglyceride selected from the group consisting of monostearoyl glycerol, monopalmitoyl glycerol, monomyrisitoyl glycerol, monocaproyl glycerol, monodecanoyl glycerol, monolauroyl glycerol, monolinoleoyl glycerol and monooleoyl glycerol, and at least one additional polyol selected from the group consisting of ethylene glycol, 1,2-propylene glycol, 1,3-propanediol, bis-2-hydroxyethyl ether, 1,4-butanediol, 1,5-pentanediol, 1,6-hexanediol, 1,8-octanediol, 1,10-decanediol, 1,12-dodecanediol, other diols, linear poly(ethylene glycol), branched poly(ethylene glycol), linear poly(propylene glycol), branched poly(propylene glycol), linear poly(ethylene-co-propylene glycol)s and branched poly(ethylene-co-propylene glycol)s.

10. The medical device of claim 1 further comprising an inorganic filler.

11. The medical device of claim 11 wherein said inorganic filler is selected from the group consisting of alpha-tricalcium phosphate, beta-tricalcium phosphate, calcium carbonate, barium carbonate, calcium sulfate, barium sulfate and hydroxyapatite.

12. The medical device of claim 10 wherein said inorganic filler comprises a polymorph of calcium phosphate.

13. The medical device of claim 10 wherein said inorganic filler is hydroxyapatite.

14. The medical device of claim 10 further comprising a therapeutically effective amount of a bioactive agent.

15. The medical device of claim 14 wherein said bioactive agent is a growth factor.

16. The medical device of claim 15 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-β I-III, growth differentiation factor, parathyroid hormone, vascular endothelial growth factor, hyaluronic acid, glycoprotein, lipoprotein, bFGF, TGF$_\beta$superfamily factors, BMP-2, BMP-4, BMP-6, BMP-12, sonic hedgehog, GDF5, GDF6, GDF8, PDGF, tenascin-C, fibronectin, thromboelastin, and thrombin-derived peptides.

17. The medical device of claim 10 further comprising a biologically derived substance selected from the group consisting of demineralized bone, platelet rich plasma, bone marrow aspirate and bone fragments.

18. The medical device of claim 1 further comprising a therapeutically effective amount of a bioactive agent.

19. The medical device of claim 18 wherein said bioactive agent is a growth factor.

20. The medical device of claim 19 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-β I-III, growth differentiation factor, parathyroid hormone, vascular endothelial growth factor, hyaluronic acid, glycoprotein, lipoprotein, bFGF, T6F$_\beta$superfamily factors, BMP-2, BMP-4, BMP-6, BMP-12, sonic hedgehog, GDF5, GDF6, GDF8, PDGF, tenascin-C, fibronectin, tispoelastin, and thromlin-derived peptides.

21. The medical device of claim 1 wherein said liquid polymer further comprises terminal and pendant chemical moieties prepared by suitable endcapping reactions.

22. The medical device of claim 21 wherein said terminal and pendant chemical moieties are selected from the group consisting of ethers, esters, anhydrides, mixed anhydrides, sulfonates, and urethanes.

23. The medical device of claim 21 further comprising an inorganic filler.

24. The medical device of claim 23 wherein said inorganic filler is selected from the group consisting of alpha-tricalcium phosphate, beta-tricalcium phosphate, calcium carbonate, barium carbonate, calcium sulfate, barium sulfate and hydroxyapatite.

25. The medical device of claim 23 wherein said inorganic filler comprises a polymorph of calcium phosphate.

26. The medical device of claim 23 wherein said inorganic filler is hydroxyapatite.

27. The medical device of claim 23 further comprising a therapeutically effective amount of a bioactive agent.

28. The medical device of claim 27 wherein said bioactive agent is a growth factor.

29. The medical device of claim 28 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-$\beta$ I-III, growth differentiation factor, parathyroid hormone, vascular endothelial growth factor, hyaluronic acid, glycoprotein and lipoprotein.

30. The medical device of claim 21 further comprising a biologically derived substance selected from the group consisting of demineralized bone, platelet rich plasma, bone marrow aspirate and bone fragments.

31. The medical device of claim 21 further comprising a therapeutically effective amount of a bioactive agent.

32. The medical device of claim 31 wherein said bioactive agent is a growth factor.

33. The medical device of claim 32 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-$\beta$ I-III, growth differentiation factor, parathyroid hormone, vascular endothelial growth factor, hyaluronic acid, glycoprotein and lipoprotein.

34. A bone replacement composition, comprising: a liquid polymer comprising the reaction product of a polybasic acid or derivative thereof, a fatty acid and a polyol, said liquid polymer comprising an aliphatic polyester backbone having fatty acid ester groups vending therefrom and said liquid polymer having a melting point less than about 40° C., as determined by differential scanning calorimetry wherein said polybasic acid or derivative thereof is selected from the group consisting of succinic acid succinic anhydride, malic acid, tartaric acid, citric acid, diglycolic acid diglycolic anhydride, glutaric acid, glutaric anhydride, adipic acid, pimelic acid, suberic acid, sebacic acid, fumaric acid, maleic acid, maleic anhydride, mixed anhydrides, esters, activated esters, and acid halides.

35. The composition of claim 34 further comprising an inorganic filler.

36. The composition of claim 35 wherein said inorganic filler is selected from the group consisting of alpha-tricalcium phosphate, beta-tricalcium phosphate, calcium carbonate, barium carbonate, calcium sulfate, barium sulfate, a polymorph of calcium phosphate and hydroxyapatite.

37. The composition of claim 34 further comprising a therapeutically effective amount of a bioactive agent.

38. The composition of claim 37 wherein said bioactive agent is a growth factor.

39. The composition of claim 38 wherein said growth factor is selected from the group consisting of cell attachment mediators, biologically active ligands, integrin binding sequence, bone morphogenic proteins, epidermal growth factor, fibroblast growth factor, platelet-derived growth factor, IGF-I, IGF-II, TGF-$\beta$ I$\beta$III, growth differentiation factor, parathyroid hormone, vascular endothelial growth factor, hyaluronic acid, glycoprotein, lipoprotein, bFGF, TGF$_\beta$superfamily factors, BMP-2, BMP-4, BMP-6, BMP-12, sonic hedgehog, GDF5, GDF6, GDF8, PDGF, tenascin-C, fibronectin, thromboelastin, and thrombin-derived peptides.

40. The composition of claim 34 further comprising a biologically derived substance selected from the group consisting of demineralized bone, platelet rich plasma, bone marrow aspirate and bone fragments.

* * * * *